(12) United States Patent
Shah et al.

(10) Patent No.: US 8,028,562 B2
(45) Date of Patent: Oct. 4, 2011

(54) HIGH PRESSURE AND HIGH TEMPERATURE CHROMATOGRAPHY

(75) Inventors: Jagdish Shah, Southington, CT (US); Neil William Bostrom, Belmont, MA (US); Oleg Zhdaneev, Cambridge, MA (US); Bhavani Raghuraman, Wilton, CT (US); Kristofer Gunnar Paso, Brooklyn Park, MN (US)

(73) Assignee: Schlumberger Technology Corporation, Cambridge, MA (US)

( * ) Notice: Subject to any disclaimer, the term of this patent is extended or adjusted under 35 U.S.C. 154(b) by 597 days.

(21) Appl. No.: 11/958,049

(22) Filed: Dec. 17, 2007

(65) Prior Publication Data

US 2009/0151426 A1  Jun. 18, 2009

(51) Int. Cl.
*G01N 30/02* (2006.01)
(52) U.S. Cl. .................................................. 73/23.35
(58) Field of Classification Search ................... None
See application file for complete search history.

(56) References Cited

U.S. PATENT DOCUMENTS

| | | | |
|---|---|---|---|
| 3,607,075 A * | 9/1971 | Wolf et al. ............... | 73/23.39 |
| 4,860,581 A | 8/1989 | Zimmerman et al. | |
| 4,936,139 A | 6/1990 | Zimmerman et al. | |
| 6,670,605 B1 * | 12/2003 | Storm et al. ............. | 250/259 |
| 7,318,343 B2 * | 1/2008 | Coenen ..................... | 73/152.19 |
| 2010/0018287 A1 * | 1/2010 | Iakimov .................... | 73/23.41 |

FOREIGN PATENT DOCUMENTS

| | | |
|---|---|---|
| WO | 01/73424 A1 | 10/2001 |
| WO | 2007/078214 A2 | 3/2007 |
| WO | 2007/076193 A1 | 7/2007 |

OTHER PUBLICATIONS

Berezkin et al, "Pressure effects on relative retention in capillary gas-liquid chromatography", J. High Resol. Chromatogr., vol. 20, Jun. 1997, pp. 333-336.
Chemistry 407 Instrumental Analysis Laboratory Manual and Supplemental Problems, University of Louisiana at Monroe, 2006.
Cussler, "Diffusion: Mass Transfer in Fluid Systems" Second Edition, "Values of Diffusion Coefficients" pp. 101-111 1997.
LS Ettre, "Open tubular columns prepared with very thick liquid phase film I. Theoretical basis", Chromatographia, vol. 17, No. 10, Oct. 1983, pp. 553-559.

(Continued)

*Primary Examiner* — Hezron E Williams
*Assistant Examiner* — Alex Devito
(74) *Attorney, Agent, or Firm* — Rachel E. Greene; Brigid Laffey

(57) ABSTRACT

Methods and related systems are described for high pressure chromatographic analysis. The described system includes a flowpath adapted to flow a mobile phase and the sample at high pressures, an injector adapted to inject the fluid sample into a flowpath, a separation column adapted to operate at high pressures for separating various components, a detector and a processor that calculates the amount of at least one component of the fluid sample. The system can operate a pressures above 20 atm or even 100 atm, and temperatures above about 100 degrees Celsius. The system can deployed in a wellbore in a subterranean rock formation, and include fluid collection system for obtaining the fluid sample downhole. The system can also be located close to a wellhead and includes a tap in fluid communication with a surface flowline carrying produced fluids and the injector.

48 Claims, 11 Drawing Sheets

OTHER PUBLICATIONS

Ettre et al, "Open tubular columns prepared with very thick liquid phase film II. investigations on column efficiency", Chromatographia, vol. 17, No. 10, Oct. 1983, pp. 560-569.

AC Frost, "A method for the measurement of binary gas diffusivities", PhD. Thesis, Chapter VI, Columbia University, 1967, University Microfilms, Inc., Ann Arbor, Michigan.

Fuller et al, "A comparison of methods for predicting gaseous diffusion coefficients", J. of Gas Chromatography, Jul. 1965, pp. 222-227.

Gonzalez et al, "Distribution coefficients of n-alkanes measured on wall-coated capillary columns", Journal of Chromatography, A, 879 (2000), pp. 157-168.

Grushka et al, "Measurement of diffusion coefficients of octane isomers by the chromatographic broadening method", The Journal of Physical Chemistry, vol. 77, No. 11, 1973, pp. 1437-1442.

Hargrove et al, "Determination of gaseous interdiffusion coefficients for solute vapor-carrier gas pairs", Analytical Chemistry, vol. 39, #2, 1967, pp. 244-246.

Hierlemann et al, "Conferring selectivity to chemical sensors via polymer side-chain selection: thermodynamics of vapor sorption by a set of polysiloxanes on thickness-shear mode resonators", Analytical Chemistry, vol. 72, No. 16, Aug. 15, 2000, pp. 3696-3708.

Hierlemann et al, "Use of linear solvation energy relationships for modeling responses from polymer-coated acoustic-wave vapor sensors", Analytical Chemistry, vol. 73, No. 14, Jul. 15, 2001, pp. 3458-3466.

Hinshaw et al, "The variation of carrier gas viscosities with temperature", J. High Resol. Chromatogr., vol. 20, #9, Sep. 1997, pp. 471-481.

Kwa, "High-pressure gas chromatography: I. A precision high-pressure gas chromatograph for isobaric isothermal measurements" Journal of Chromatography, vol. 270, 1983, pp. 105-115.

Marrero et al, "Gaseous diffusion coefficients", J. Phys. Chem. Ref. Data., vol. 1, No. 1, 1972, pp. 79-80.

Poling et al, "Diffusion in multicomponent gas mixtures", The Properties of Gases and Liquids, Fifth Edition, 2001, chapter 11-7, pp. 11.19-11.20.

Pompe et al, "Prediction of thermodynamic parameters in gas chromatography from molecular structure: hydrocarbons", J. Chem. Inf. Comput. Sci., 2004, vol. 44, pp. 399-409.

Purnell, "Comparison of efficiency and separating power of packed and capillary gas chromatographic columns", Nature, Dec. 26, 1959, vol. 184, suppl. 26, 2009.

Vandensteendam, Measurement of the gaseous diffusion coefficients of a homologous series of compounds in helium. Temperature funciton of n-alkanes and methyl n-alkanoates, Journal: C.R. Acad. Sci., Ser. C, 1972, vol. 274, No. 25, pp. 2032-2034.

Van Deursen, "Theoretical Aspects of High speed Gas Chromatography", Novel Concepts for Fast Capillary Gas Chromatography, Chapter 2, 2002, 37 pages.

Vezzani et al, "Prediction of retention times and efficiency in linear gradient programmed pressure analysis on capillary columns" Journal of Chromatography A, 1055, (2004) pp. 141-150.

Vorob'ev, "Diffusion questions in chemical kinetics", 2003, MSU.

Wicar et al, "Retention volume in high-pressure gas chromatography I: Thermodynamics of the specific retention volume", Journal of Chromatography, vol. 95, (1974), pp. 1-12.

Wicar et al, "Retention vol. In high-pressure gas chromatography II. Comparison of experimental data with the prediction of a pseudo-binary model", Journal of Chromatography, vol. 95, (1974), pp. 13-26.

* cited by examiner

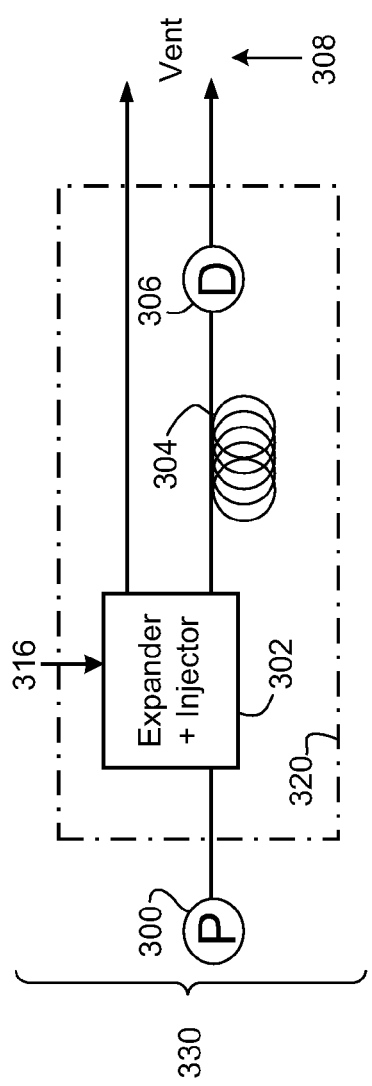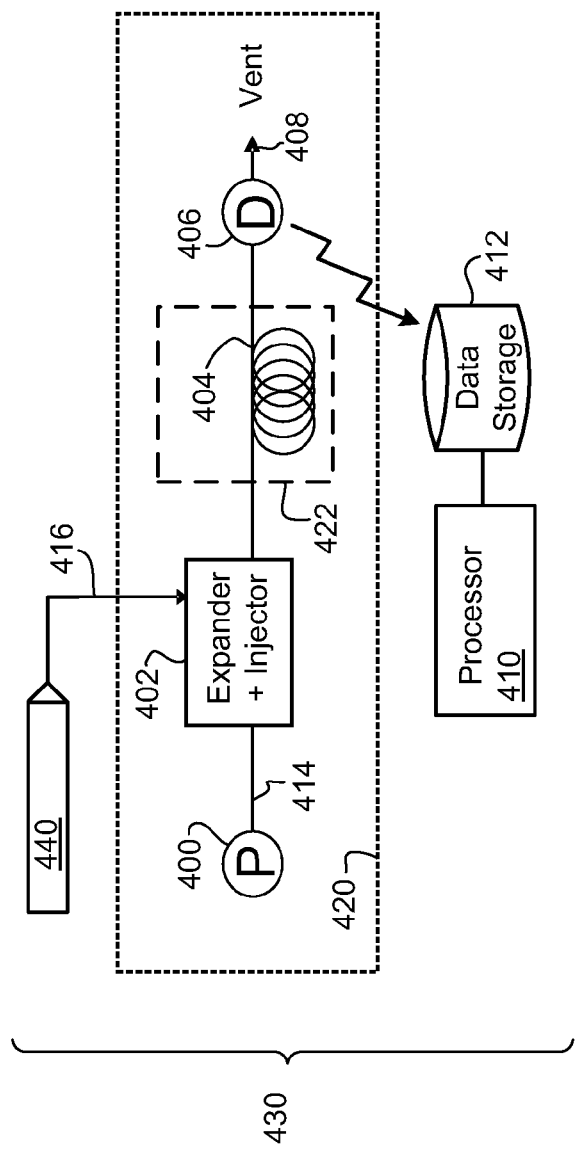

HIGH PRESSURE AND HIGH TEMPERATURE CHROMATOGRAPHY

BACKGROUND OF THE INVENTION

1. Field of the Invention

This patent specification relates to chromatography. More particularly, this patent specification relates to systems and methods for chromatography under high-pressure and/or high temperature environments.

2. Background of the Invention

Chromatography is the field of separating chemicals based on differences in properties such as volatility, absorption, adsorption, size, etc. In this field, different rates of migration along a given flow path (gas, liquid, supercritical fluid, etc) result in the spatial separation of chemical analytes. This differential migration is achieved by differing rates of interaction with the separation column or by different values of analyte mobility.

Typical gas chromatography (GC) separation columns are small diameter tubes that can be more than 15 meters long. The column, usually wound in a coil, is housed inside a heated compartment or co-wound with heater wires. The heater is designed to keep the column at either constant temperature, or for certain analyses, provide it with an increasing and fast temperature ramp. In the case of a ramped system, after a sample analysis is completed, the column must be cooled to the lower starting temperature. The cooling process can be particularly time consuming unless means of cooling such as fan, thermal switch, etc. is provided. However, the heating and cooling apparatus contributes significantly to the total mass, which makes the heating and especially the cooling function slow and inefficient.

Certain environments, such as oil and gas wells, have unusually harsh ambient conditions. For example, it is not uncommon for the ambient conditions within the borehole to be greater than about 100° C. and greater than about 100 atmospheres in pressure. In order to operate a chromatograph under such conditions, existing methods would require depressurization of sampled fluid to around 1 atmosphere, and cooling of certain components of the chromatography apparatus considerably below the ambient temperature. Such methods pose significant challenges for implementing chromatography equipment in downhole environment. Additionally, for the high temperature downhole environment, it is difficult to reject heat from the column/heater/cooler apparatus.

Samples of downhole fluids such as collected using a downhole sampling tool or collected on the surface very close to the wellbore are typically stored in bottles and shipped to laboratories for analysis. This transportation process to the laboratory takes a significant amount of time which can be very costly for some applications such as off shore operations. Additionally, the sample at the laboratory, in order to be analyzed using convention chromatography systems, needs to be depressurized. The process is sometimes complex and during transportation, handing and preparation the pressure and temperature changes can induce significant changes in the chemical properties of the sample prior to analysis.

Some research has been published on the relationship of high pressures to the retention times in chromatography. For example, T. L. Kwa, *High-pressure gas chromatography: I. A precision high-pressure gas chromatograph for isobaric-isothermal measurements*, Journal of Chromatography A, Vol. 270, 1983, P. 105-115 discloses a high pressure chromatograph with a packed column used to investigate thermodynamic and transport properties of certain fluids. In another example, Viktor B. Berezkin, Alexander A. Korolev, and Irina V. Malyukova, *Pressure effect on Relative Retention in Capillary Gas-Liquid Chromatography*, J. High Resol. Chromatogr., 1997, Vol. 20, June, P. 333-336 discloses experiments up to about 10 atmospheres to understand the dependence of relative retention and retention indexes on average column pressure. However, these prior systems and methods were primarily concerned with understanding pressure relationships with retention time and did not attempt to propose any techniques for optimizing resolution at high pressures.

SUMMARY OF THE INVENTION

According to embodiments, a system for chromatographic analysis of a sample containing a plurality of components is provided. The system includes a flowpath adapted to flow a mobile phase and the sample at high pressures; an injector adapted to inject the fluid sample into a flowpath; a separation column adapted to operate at high pressures, forming part of the flowpath downstream of the injector, for separating a plurality of components within the fluid sample; a detector located downstream of the column, thereby generating measurement data representing properties of at least one component of the fluid sample; and a processor adapted calculate from the measurement data a value relating to the amount of at least one component of the fluid sample. According to certain embodiments, the system can operate a pressures above 20 atm or even 100 atm, and temperatures above about 100 degrees Celsius. According to certain embodiments the system also includes a tool housing constructed and adapted to be deployed in a wellbore in a subterranean rock formation; and a fluid collection system for obtaining the fluid sample downhole, wherein the flowpath, injector, column and detector are housed within the tool housing and adapted to operate under downhole conditions. According to other embodiments, the system is in close proximity to a wellhead and includes a tap in fluid communication with a surface flowline carrying produced fluids and the injector.

According to embodiments, a method for high pressure chromatographic analysis of a sample containing a plurality of components is provided. The method includes injecting the sample into a high pressure flowpath; flowing the injected sample through a separation column; detecting a property of the fluid in the flow path with a detector thereby generating measurement data; and calculating from the measurement data a value relating to the amount of at least one component of the fluid sample.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 3 shows a chromatography system according to an embodiment;

FIG. 4 shows further detail for a chromatographic analysis system, according to embodiments;

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

Figure 1:
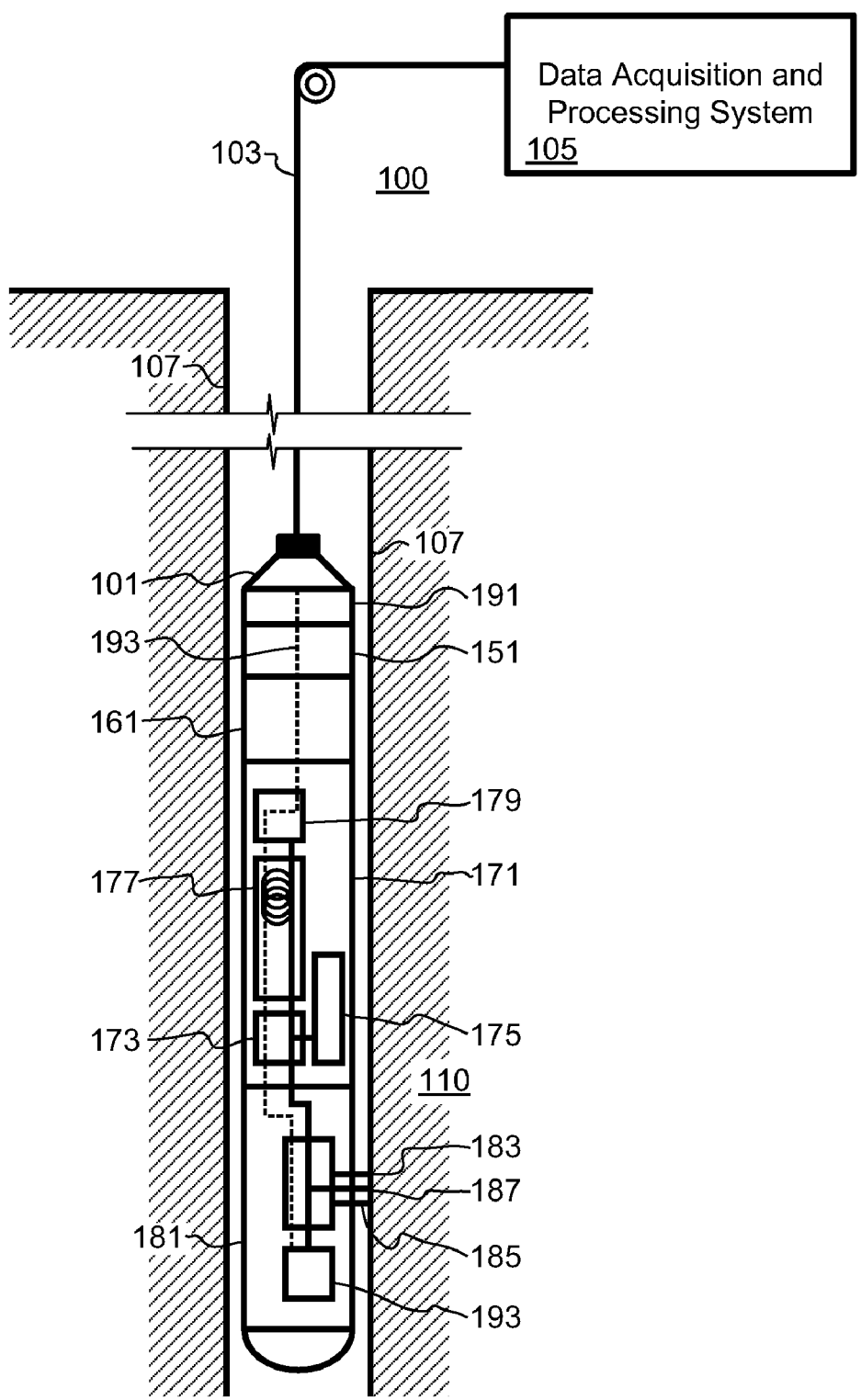
FIG. 1 shows a downhole system for chromatographic analysis of a downhole collected fluid sample, according to embodiments.

FIG. 1 shows a downhole system for chromatographic analysis of a downhole collected fluid sample, according to embodiments. Wireline logging system 100 has a chromatographic analysis tool 171. In wireline well logging, one or more tools containing sensors for taking geophysical measurements are connected to a wireline 103, which is a power and data transmission cable that connects the tools to a data acquisition and processing system 105 on the surface. The tools connected to the wireline 103 are lowered into a well borehole 107 to obtain measurements of geophysical properties for the surrounding subterranean rock formation 110. The chromatographic analysis system 171 can be part of a tool string 101 comprising several other tools 151, 161 and 181. The wireline 103 supports tools by supplying power to the tool string 101. Furthermore, the wireline 103 provides a communication medium to send signals to the tools and to receive data from the tools.

The tools 151, 161, 171 and 181 are typically connected via a tool bus 193 to telemetry unit 191 which is turn is connect to the wireline 103 for receiving and transmitting data and control signals between the tools 151, 161, 171, 181 and the surface data acquisition and processing system 105. Commonly, the tools are lowered to a particular depth of interest in the borehole and are then retrieved by reeling-in by the data acquisition and processing system 105. As the tools are retrieved from the well borehole 107, the tools collect and send data via wireline 103 about the geological formation through which the tools pass to data acquisition and processing system 105 at the surface, usually contained inside a logging truck or logging unit (not shown).

Fluid sampling unit 181 is shown having probe 183 with intake 187 and flowline 185. Fluid sampling unit 181 also typically includes a pump (not shown) and sample chamber 193. Alternatively, a pair of packers (not shown) may be used in place of the probe. Examples of a fluid sampling system using probes and packers are depicted in U.S. Pat. Nos. 4,936,139 and 4,860,581 where are incorporated by reference herein. The flowline 185 connects the intake 187 the sample chamber 193, pump and chromatographic analysis unit 171. Fluid is selectively drawn into the tool through the intake 187 by activating the pump to create a pressure differential and draw fluid into the sampling unit 181. As fluid flows into the tools, fluid is preferably passed from flowline 27 into sample the sample chamber 193. Additional valves, restrictors or other flow control devices may be used as desired.

For chromatographic analysis, the fluid is drawn into chromatographic analysis unit 171 via flowline 185. The fluid that is to be chromatographically analyzed can be either drawn directly from the formation 110 via intake 187, or it can be from the sample chamber 193. Injector 173 introduces a small sample of the fluid to be analyzed into a stream of carrier gas from carrier gas storage 175. Injector 173 is also deemed to perform the function of converting the sample into gas phase. This combined stream of sample gas and carrier gas then flow via flowline 174 to passes through separation column 177, which performs a time-based elution of the components of the sample. Detector 179 provides a time history of the presence and relative concentration of each eluted component. The resulting data is passed to data acquisition and processing system 105 via telemetry unit 191. In the data acquisition and processing system 105, the data is interpreted as a chromatogram consisting of a series of peaks, each representing a specific component, while the area under the peak provides a measure of the quantity of that component in the sample. The area under the peak can be used to provide a measure for the mass concentration of one or more of the components, the volume concentration of one or more of the components, or the ratio of components.

Figure 2:
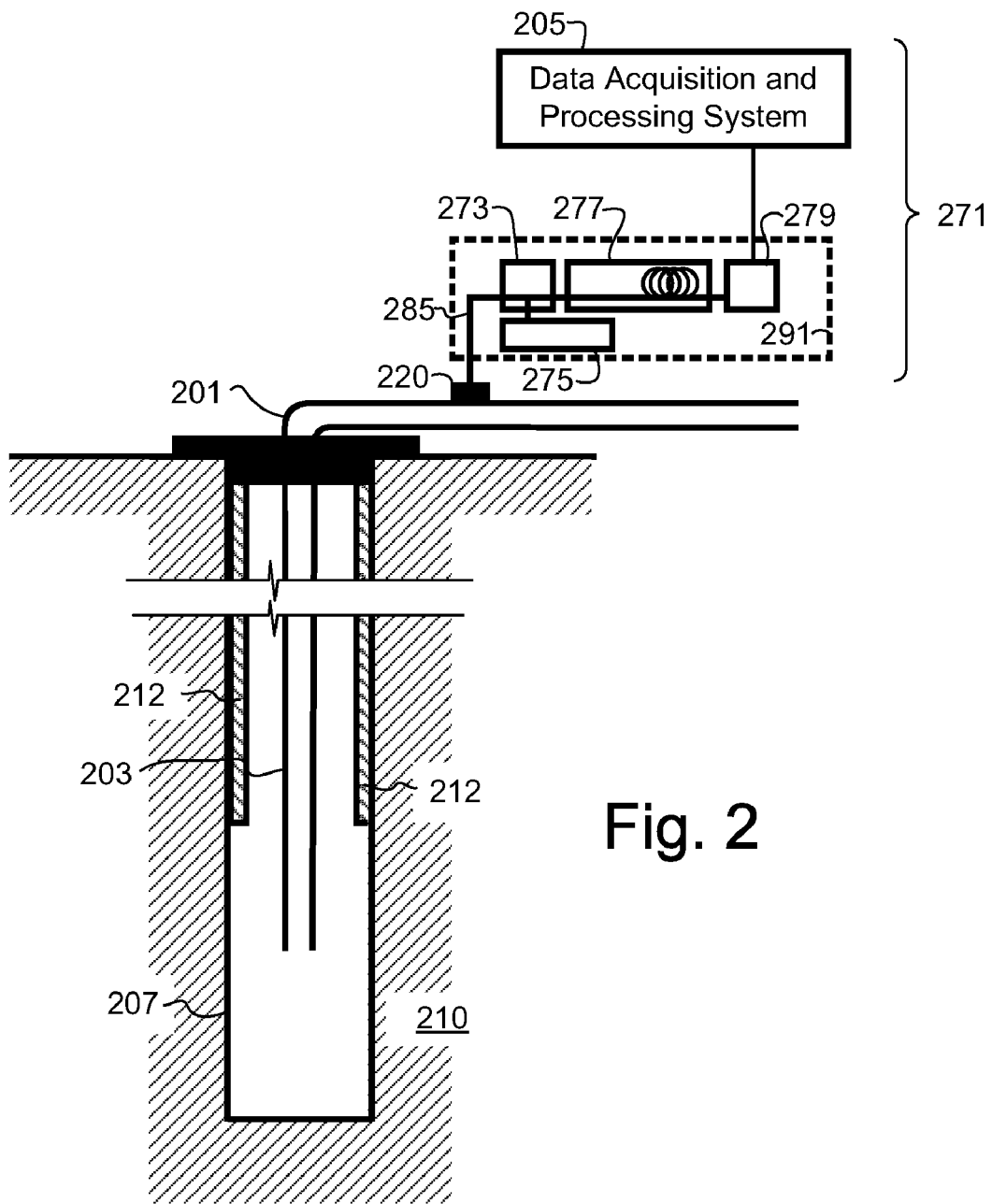
FIG. 2 shows a system for chromatographic analysis of wellbore fluids, according to embodiments.

FIG. 2 shows a system for chromatographic analysis of wellbore fluids, according to embodiments. Well borehole 207 is shown within subterranean rock formation 210. Wellbore fluids are produced from formation 210 and are drawn into production tubing 203 via a drawdown pressure differential between the formation 210 and tubing 203. Borehole 207 can be completed with a casing 212 that provides wellbore stability and zonal isolation via cement (not shown). Alternatively, the fluids can be produced through perforations in a casing from specific zones (not shown). At the surface, production tubing 203 passes through wellhead 201 and is connected to a surface distribution system (not shown). Chromatographic analysis system 271 is provided close to the wellhead 201 and obtains a sample of the fluid via tap 220 and flowline 285. Injector 273 introduces a small sample of the fluid to be analyzed into a stream of carrier gas from carrier gas storage 275. Injector 273 is also deemed to perform the function of converting the sample into gas phase. This combined stream of sample gas and carrier gas then flow via flowline 274 to passes through separation column 277, which performs a time-based elution of the components of the sample. Detector 279 provides a time history of the presence and relative concentration of each eluted component. The resulting data is passed to data acquisition and processing system 205. In the data acquisition and processing system 205, the data is interpreted as a chromatogram consisting of a series of peaks, each representing a specific component, while the area under the peak provides a measure of the quantity of that component in the sample. Due to the pressure differential between the wellbore fluid being analyzed and the ambient pressure, and depending up to the embodiment, a pressurized enclosure 291 can also be provided to balance the pressure surrounding injector, column and detector with the pressure of the sampled fluid. Enclosure 291 preferably uses a nitrogen gas source for pressurization (not shown). Note that in an alternative embodiment, a pressurized enclosure similar to enclosure 291 can be provided within chromatographic analysis unit 171 shown in FIG. 1.

For chromatography of oils, it is a common practice to heat the column gradually and ramp up its temperature from around 30° C. to higher than 300° C., while the injector and the detector are heated to greater than 100° C., usually 250° C.-300° C. continuously in order to perform efficient analysis. In preparation for subsequent analysis, the column is cooled down again to around 30° C. The absolute pressure of the system (i.e. injector, column, detector etc.) is also kept at approximately 1 atmosphere during the analysis.

However these techniques cause complications when applied to downhole analysis as shown in the embodiment of FIG. 1. In oil wells, temperatures in the range of 100° C. to 200° C. and pressures of 5,000 to 20,000 psi often exist (340 atm to 1361 atm). FIG. 3 shows a chromatography system according to an embodiment. Chromatography system 330 can either be placed in a borehole such as unit 171 in FIG. 1 or on the surface near a well head such as system 271 in FIG. 2. In the case of borehole placement, cooling device 320 is provided to carry out chromatographic analysis at standard pressures and temperatures. Cooling device capable of achieving temperature drop of up to 170° C. However, providing a cooling effect of such large differential temperature is challenging in a oil well because there is no easy way to transfer heat. Therefore the chromatography system 330 is best suited for placement in boreholes with relatively cool temperatures, or on the surface near the borehole.

The downhole collected fluid to be analyzed is normally at reservoir pressure, which could be as high as 20,000 psi. (1361 atmospheres). Expander injector 302 is provided to bring the sample 316 down to about 1 atmosphere. Since the sample evaporation into gas phase in expander injector 302 results in a large volume of gas, only a small portion of which is actually injected into the column, with the rest being deposited to waste, via vent 308. The reduced pressure and temperature injected sample is then carried through the flowpath by mobile phase source 300, through column 304 and the separated components are detected and measured by detector 306 before passing to vent 308. Data from detector 306 are stored in data storage and processing system (not shown).

FIG. 4 shows further detail for a chromatographic analysis system, according to embodiments. Chromatography system 430 had the capability to operate at high pressures and high temperatures for more effective chromatographic analysis in locations such as in a borehole, such as unit 171 in FIG. 1, and at a wellhead, such as system 271 in FIG. 2. It has been found that chromatographic system as shown in FIG. 4 can be much simpler and more effective than system 330 shown in FIG. 3 for many oilfield applications. Flowpath 414 from mobile phase source 400, through expander/injector 402, column 404 to detector 406 is maintained at pressures much closer to the incoming sample 416. Heater/cooler 422 can raise and lower the temperature of the column 404. Additionally, there are typically heaters (not shown) associated with injector 402, detector 406 the interconnecting flowlines. This high-pressure chromatographic system significantly reduces the volume of wastes associated with reducing the pressure by such large amounts as in system 330 of FIG. 3. For example, a sample pressure is reduced to around 3000 psi (or ~200 atm). The resulting gas has a volume only 15% of the volume of a low pressure (i.e. about 1 atm) system. The resulting waste stream from the high pressure column is only 15% by volume compared to a lower pressure one. This makes storing waste locally within the chromatogram in a space-efficient manner much less complex. Alternatively, a much smaller amount of compression is needed if rejection into the well is desired, thus reducing the size of the expander, the compressor and corresponding power needs. Sample 416 flows from sample bottle 440 which preferably maintains the sample at pressures and temperatures similar to those in the rock formation from which the sample was collected. In the downhole environment, the sample bottle 440 can be the sample chamber 193 as shown in FIG. 1, or alternatively the sample can flow directly from the formation without being stored in a bottle. On the surface, sample bottle 440 can be a chamber similar to sample chamber 193 that is transportable while maintaining the sample at high pressures and/or temperatures for later analysis. Alternatively, the sample 416 can flow directly from a flowline on the surface such as flowline 285 from tap 220 as shown in FIG. 2.

The components of system 430, being exposed to high pressures should be selected and adapted to withstand such pressures. For example, stainless steel tubing is preferable for use in separation column 404. Additionally, to compensate for stress on flowpath 414, injector 402, column 404 and detector 406, a pressure balancing enclosure 420 may be provided, such as enclosure 291 shown in FIG. 2. It has also been found that effective chromatographic analysis can be performed at much higher temperatures such that the cooling system, if included, is much less complex than for system 330 of FIG. 3. Furthermore, it has been found that chromatography under high pressure and high temperature environments actually in some cases leads to higher quality chromatograms due to sharper peak definitions.

The measurements from detector 406 are transmitted to data storage 412 and also to processor 410. Processor 410 and data storage 412 can be part of a system such as data acquisition and processing systems 105 and 205 shown in FIGS. 1 and 2 respectively. In Processor 410, the data is interpreted as a chromatogram consisting of a series of peaks, each representing a specific component, while the area under each peak provides a measure of the quantity of that component in the sample. The area under the peak is used to calculate values related to the amount of the components such as: a measure for the mass concentration of one or more of the components, the volume concentration of one or more of the components, and/or the ratio of components.

Figure 5:
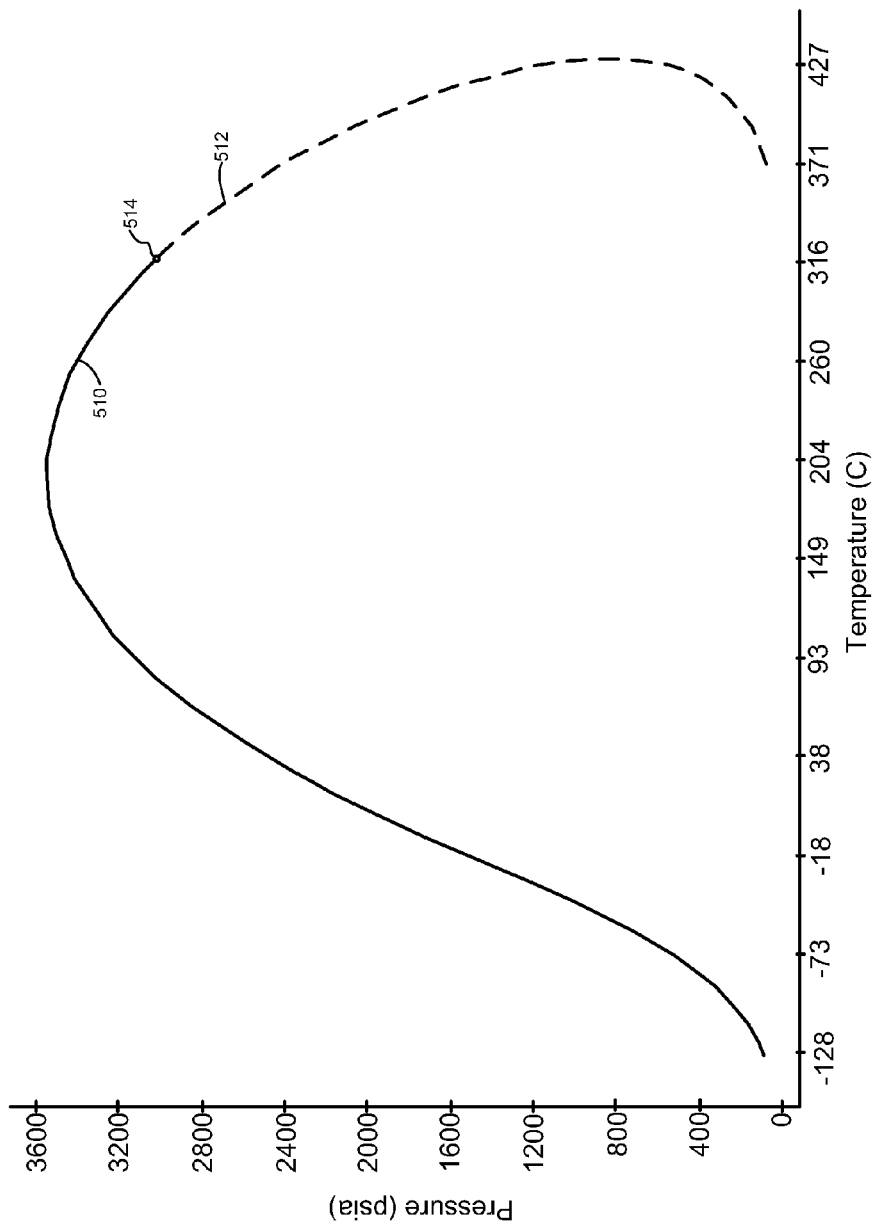
FIG. 5 is a graph showing a typical phase relationship with respect to pressure and temperature of black oil.

FIG. 5 is a graph showing a typical phase relationship with respect to pressure and temperature of black oil. The solid curve 510 is the bubble point, the broken curve 512 is the dew point, and the point 514 is the critical point. Commonly, oil well temperatures are below 200 C and pressure below 20,000 psi. If a sample of oil with a collected within such an oil well having a phase relationship as shown in FIG. 5 were manipulated such that its temperature and pressure plot above the dew point curve 512, it would transition to gas phase, and could then be introduced into a separation column. In some cases moving to a point above the dew point curve could be achieved by a rapid rise in temperature provided by the heater on the injector/evaporator. In other cases the rise in temperature can be combined with a drop in pressure. Although the phase envelope may differ for different types of formation fluids, chromatography above well bore temperature and at high pressures is generally possible. Operating a chromatogram at as high a pressure as possible and temperature above the ambient has distinct advantages as described below.

With the system 430 shown in FIG. 4, when chromatographic separation is done at temperatures above the ambient, a cooling device is not necessary. The components of the chromatograph are heated to >200° C., and may involve a temperature ramp from 200° C. to 350° C. or more. In preparation for the next analysis, these components need to be cooled down again to 200° C., still above the well bore temperature. However, this is achieved by simply rejecting the heat to the well, since it is below 200° C.; the well is used as a heat sink. Natural cooling, which may be assisted by a fan (not shown), can perform the heat rejection. The elimination of a cooling sub-system is significantly advantageous because it results in a simpler and less expensive tool design. Space and power are also saved by this approach, which eliminates hefty cooling components. By starting at a high initial temperature, the system shown in FIG. 4 can perform chromatographic analysis at ambient temperatures above 75° C. Preferably, the system can perform chromatography above 100° C., and even more preferably above 150° C. Furthermore, it has been found from the evaluations described herein that even where the ambient temperature is relatively low, such as with normal surface temperatures, the chromatography system such as shown in FIG. 4 can benefit from starting at a relatively high column temperature. For example, heater 422 can be used to provide a temperature of 100° C. on column 404 when the sample first enters the column. A temperature program is then used to further raise the column temperature while the sample is flowing through the column. Apart from advantages in preserving chemical properties in the sample, using a high initial column temperature can also be useful, for example to speed up processing time in since the column can be quickly cooled down if the starting temperature is substantially higher than the ambient temperature. According to a preferred embodiment, the starting column temperature is at least 125° C., and even more preferably at least 150° C.

Operating a gas chromatograph at high pressure conditions has distinct advantages for the analysis of retrograde gases which condense when pressure conditions are reduced. If a large pressure drop is utilized within the downhole or surface chromatography unit, significant condensation of the sample can occur before injection into the gas chromatography column, resulting in an unrepresentative analysis of the initial retrograde gas composition. In addition, condensation of retrograde gases within the tool may result in significant contamination of the gas sampling lines within the tool. A contaminated gas sampling line would result in the mixing of condensed liquids and gases from various samplings, ultimately invalidating any subsequent analyses. Operation of the gas chromatography at high internal pressure condition greatly mitigates the problem of internal condensation of retrograde reservoir gases. If the internal pressure condition within the tool can be varied during the chromatography operation, knowledge of the pressure-temperature phase behavior envelope of the retrograde gas is beneficial in selecting an appropriate operating pressure/temperature of the gas chromatograph such that condensation can be avoided.

It has been found that high pressure, in some cases, increases peaks resolution while dramatically reducing the measurement time. Furthermore, while it has been found that elevated temperature also reduces measurement time, in some cases there is an upper temperature limit for the temperature in order to obtain certain amounts of desired peaks resolution.

Results of modeling for high pressure and high temperature chromatography will now be discussed in further detail to aid in optimizing chromatographic performance for particular applications. The modeling results that are based on the modeling approach where the Golay equation is used for the evaluation of pressure and temperature influence on gas chromatography performance. In particular, a modified Golay-Giddings approach is used. The Golay-Giddings equation provides predictions of theoretical plate height ("separation power") for varying mobile phase velocities:

$$HETP = \frac{B}{v_{out}} + C_m \cdot v_{out} + C_{st} \cdot v_{out} + E \cdot v_{out}^2 \tag{1}$$

Figure 6:
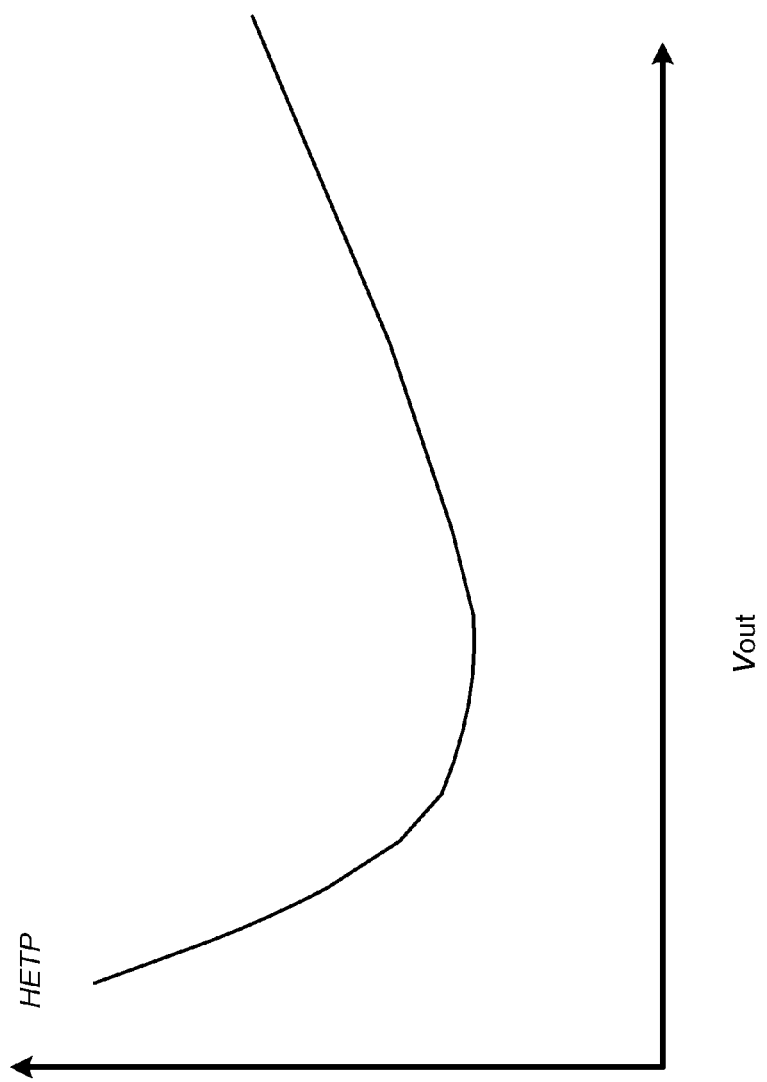
FIG. 6 is a typical plot of HETP versus the linear velocity.

The term B accounts for longitudinal diffusion, while the terms $C_{st}$ and $C_m$ account for stationary and mobile phase mass transfer resistances, and E term represents extra-column dispersion. Specifically, $$B = 2 \cdot D_m(T, p) \cdot j_1 \tag{2}$$

$$C_{st} = \frac{2}{3} \cdot \frac{k(T, p)}{(1 + k(T, p))^2} \cdot \frac{d_f^2}{D_{st}(T, p)} \cdot j_2 \tag{3}$$

$$C_m = \frac{1 + 6 \cdot k(T, p) + 11 \cdot k(T, p)^2}{24 \cdot (1 + k(T, p))^2} \cdot \frac{R_{column}^2}{D_m(T, p)} \cdot j_1 \tag{4}$$

$$E = \frac{\sigma_{extra-column}^2}{L_{column} \cdot (1 + k(T, p))^2} \tag{5}$$

where $D_m$ and $D_{st}$ are the hydrocarbon diffusivity in the gas and stationary phases, k is the retention factor, $d_f$ represents the thickness of the stationary phase, and $R_{column}$ represents the column inner radius, and $j_1$, $j_2$ are the pressure compressibility factors:

$$j_1 = \frac{9}{8} \cdot \frac{(\gamma^2 - 1) \cdot (\gamma^4 - 1)}{(\gamma^3 - 1)^2}, \tag{6}$$

$$j_2 = \frac{3}{2} \cdot \frac{(\gamma^2 - 1)}{(\gamma^3 - 1)}, \tag{7}$$

where γ is the inlet/outlet pressure ratio. FIG. 6 is a typical plot of HETP versus the linear velocity.

To calculate how the HETP will change with pressure, temperature and other parameters we need to take into account change in outlet velocity as well and the actual Golay-Giddings equation can be modified:

$$HETP(T, p) = 2 \cdot D_m(T, p) \cdot j_1 \cdot \left(\frac{R_{column}^2 \cdot p_{out}}{16 \cdot \eta_{He}(T, p) \cdot L_{column}} \cdot (\gamma^2 - 1)\right)^{-1} + \tag{8}$$

$$\ldots + \frac{1 + 6 \cdot k(T, p) + 11 \cdot k(T, p)^2}{24 \cdot (1 + k(T, p))^2} \cdot \frac{R_{column}^2}{D_m(T, p)} \cdot$$

$$\left(\frac{R_{column}^2 \cdot p_{out}}{16 \cdot \eta_{He}(T, p) \cdot L_{column}} \cdot (\gamma^2 - 1)\right) \cdot j_1 + \ldots + \frac{2}{3} \cdot \frac{k(T, p)}{(1 + k(T, p))^2} \cdot$$

$$\frac{d_f^2}{D_{st}(T, p)} \cdot \left(\frac{R_{column}^2 \cdot p_{out}}{16 \cdot \eta_{He}(T, p) \cdot L_{column}} \cdot (\gamma^2 - 1)\right) \cdot j_2 + \ldots +$$

$$\frac{\sigma_{extra-column}^2}{L_{column} \cdot (1 + k(T, p))^2} \cdot \left(\frac{R_{column}^2 \cdot p_{out}}{16 \cdot \eta_{He}(T, p) \cdot L_{column}} \cdot (\gamma^2 - 1)\right)^2$$

The variables in HETP equation are function of pressure, temperature, stationary phase thickness, and column radius. Using the expression presented above influence of pressure and temperature on the peak width can be predicted and investigated. Peak widths are related to the theoretical plate height that indicates separation power of the GC system:

$$HETP = \frac{L_{column}}{N} \text{ and } N = 16 \cdot \left(\frac{t_R}{w_b}\right)^2 \quad (9)$$

where N is the number of theoretical plates of height HETP in a column of length $L_{column}$; $w_b$ represents peak width and $t_R$ represents retention time.

Knowing carrier gas (Helium, for example) outlet velocity the required time to perform full GC analysis of the mixture if we know the value of retention coefficient for the last eluted peak can be estimated:

$$t_{min} = \frac{L_{column}}{v_{opt} \cdot j_2} \cdot (1 + k_{max}). \quad (10)$$

Based on equations 9 and 10 or in more general form using the Purnell equation (See, J. H. Purnell, *Comparison of efficiency and separating power of packed and capillary gas chromatographic column*, Nature (London), Vol. 184, Suppl. 26, P. 2009, 1959):

$$R_s = \frac{1}{4} \cdot \sqrt{\frac{L}{HETP_{min}}} \cdot \left(\frac{\alpha - 1}{\alpha}\right) \cdot \left(\frac{k}{k+1}\right), \quad (11)$$

where α is the ratio of retention times or partition coefficients of two the closest components of the mixture (in our case it was n-hexane and n-heptane) and k is the retention factor of the first component from this pair, the peaks resolution can be estimated.

Peaks resolution is the major parameter that describes the quality of chromatogram but in case of downhole operation the measurement time is also an extremely important parameter. The influence of pressure and temperature on these two factors has been investigated with described model. The first step is understanding the influence of pressure and temperature on the coefficients in the modified Golay-Giddings. Golay-Giddings equation in the form as it is presented above contains retention factors k that is related to partition coefficients K through volumetric ratio of mobile and stationary phases. Dependence of partition coefficient from temperature was computed from experimental results, calculated using Pro ezGC software (see, M. Pompe, J. M. Davis, C. D. Samuel, *Prediction of thermodynamic parameters in gas chromatography from molecular structure: hydrocarbons*, J. Chem. Inf. Comput. Sci., 2004, Vol. 44, P. 399-409), and found in literature (see Andreas Hierlemann, Edward T. Zellers, and Antonio J. Ricco, *Use of Linear Solvation Energy Relationships for Modeling Responses from Polymer-Coated Acoustic-Wave Vapor Sensors*, Anal. Chem. 2001, 73, 3458-3466; Andreas Hierlemann, Antonio J. Ricco, Karl Bodenhofer, Andreas Dominik, and Wolfgang Gopel, *Conferring Selectivity to Chemical Sensors via Polymer Side-Chain Selection: Thermodynamics of Vapor Sorption by a Set of Polysiloxanes on Thickness-Shear Mode Resonators*, Anal. Chem., 2000, Vol. 72, P. 3696-3708; and F. R. Gonzalez, L. G. Gagliardi, *Distribution coefficients of n-alkanes measured on wall-coated capillary columns*, J. of Chromatography A, 2000, Vol. 879, P. 157-168).

First, from experimental data with 90 μm diameter column, 10 m length and 2 μm thickness of stationary phase for n-octane:

$$K(T) = \exp\left(\frac{3662}{T} - 5.797\right);$$

Second, from literature for n-octane:

$$K(T) = \exp\left(\frac{4785}{T} - 8.33\right),$$

the discrepancy between literature and experimentally obtained value can be explained by the different type of PDMS that were used in our GC system.

For our calculation partition coefficients obtained from experimental data is used. From experiments with 125, 150, and 200° C. the partition coefficients for n-hexane, n-heptane, n-decane, n-dodecane, n-tetradecane were determined:

$$K_{C_6H_{14}}(T) = \exp\left(\frac{2831}{T} - 4.884\right);$$

$$K_{C_7H_{16}}(T) = \exp\left(\frac{3251}{T} - 5.35\right);$$

$$K_{C_{10}H_{22}}(T) = \exp\left(\frac{4520}{T} - 6.819\right);$$

$$K_{C_{12}H_{26}}(T) = \exp\left(\frac{5396}{T} - 7.907\right);$$

$$K_{C_{14}H_{28}}(T) = \exp\left(\frac{6232}{T} - 8.541\right).$$

There are papers where analysis of partition coefficient dependence from pressure were investigated. For example see, Viktor B. Berezkin, Alexander A. Korolev, and Irina V. Malyukova, *Pressure effect on Relative Retention in Capillary Gas-Liquid Chromatography*, J. High Resol. Chromatogr., 1997, Vol. 20, #June, P. 333-336 (hereinafter "Berezkin"); T. L. Kwa, *High-pressure gas chromatography: I. A precision high-pressure gas chromatograph for isobaric-isothermal measurements*, Journal of Chromatography A, Vol. 270, 1983, P. 105-115 (hereinafter "Kwa"); Stanislav Wičar and Josef Novák, *Retention volume in high-pressure gas chromatography: I. Thermodynamics of the specific retention volume*, Journal of Chromatography A, Volume 95, Issue 1, 31 Jul. 1974, Pages 1-12 (hereinafter "Wičar I"); Stanislav Wičar and Josef Novák, *Retention volume in high-pressure gas chromatography: II. Comparison of experimental data with the prediction of a pseudo-binary model*, Journal of Chromatography A, Volume 95, Issue 1, 31 Jul. 1974, Pages 13-26 (hereinafter "Wičar II"); and S. Vezanni, P. Moretti, G. Castello, *Prediction of retention times and efficiency in linear gradient programmed pressure analysis on capillary columns*, J. Chromatogr. A, Vol. 1055, 2004, P. 141-150 (hereinafter "Vezanni"). It was shown in Berezkin that retention coefficient can be expressed as:

$$k = k_0 - b_k \cdot P_{av} \quad (12),$$

where $k_0$ is the retention coefficient obtained by extrapolating to "zero" pressure, and $b_k$ is the coefficient that is proportional to the retention factors of sorbates and is dependent on stationary phase thickness and the nature of stationary phase, temperature. To the best of our knowledge there are no available data for $b_k$ coefficient for PDMS for different film thicknesses and values of retention factors but the most important conclusion is that retention coefficient will decrease when the pressure will increase.

According to the experimental results published in Berezkin for several organic compounds the retention coefficient value will drop by 0.6% when the pressure will raise from 1 atm to 100 atm in case where the retention coefficient equals 0.739 and by 22.6% in case where retention coefficient equals 9.724. At elevated temperature of standard downhole conditions, the retention coefficient will be significantly smaller compared to coefficient at ambient surface temperatures. This is another reason why the change in retention coefficient is small. In Wičar II results are presented for isooctane solute with hydrogen as a carrier gas at 50 and 75° C. According to Wičar II the retention coefficient will drop by 33% when pressure increases from 10.6 to 97.7 atm at 50° C., and by 29% at 75° C. Note that in the case of nitrogen the changes in partition coefficient were significantly bigger (more than 50%). In cases of such a change of retention coefficient it is possible to mitigate this effect changing stationary phase type or varying the temperature. Accordingly, increasing pressure will in general result in small relative reductions in retention factors.

Figure 7A:
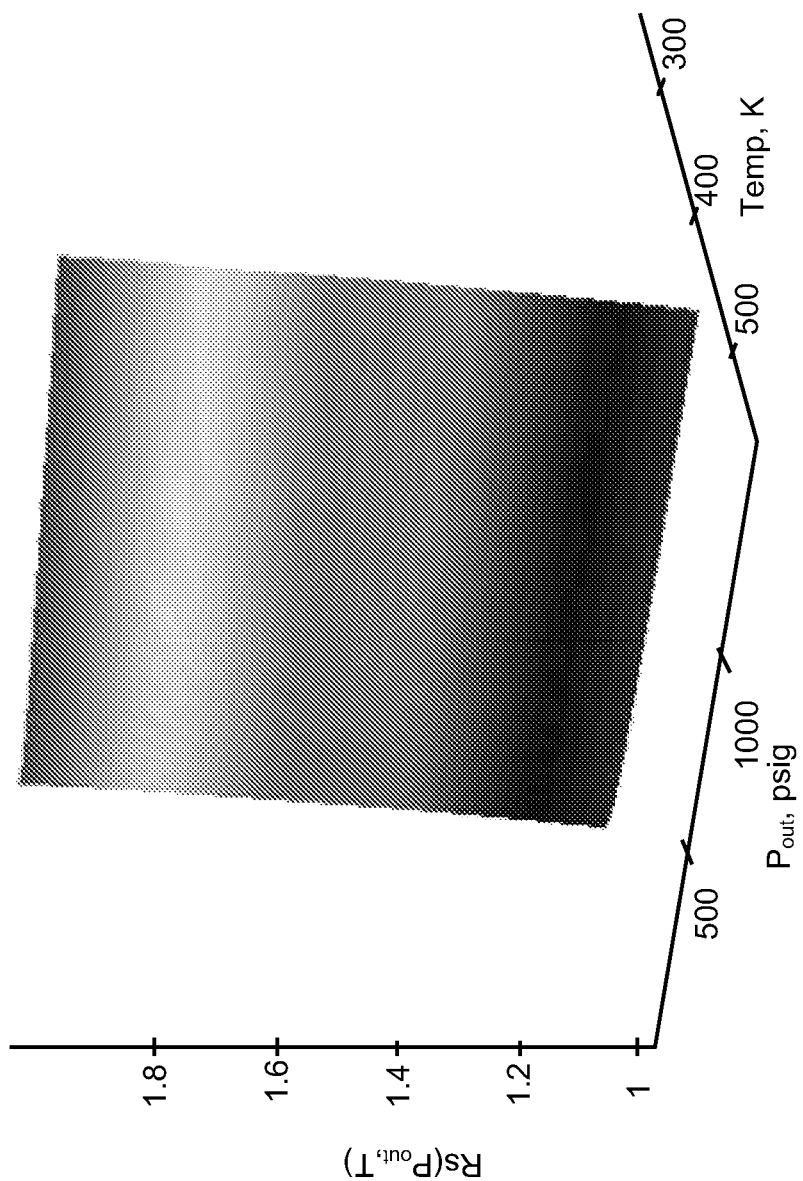
FIGS. 7a and 7b are graphs showing sensitivity of peaks resolution as a function of outlet pressure and temperature for n-hexane and n-heptane.
Figure 7B:
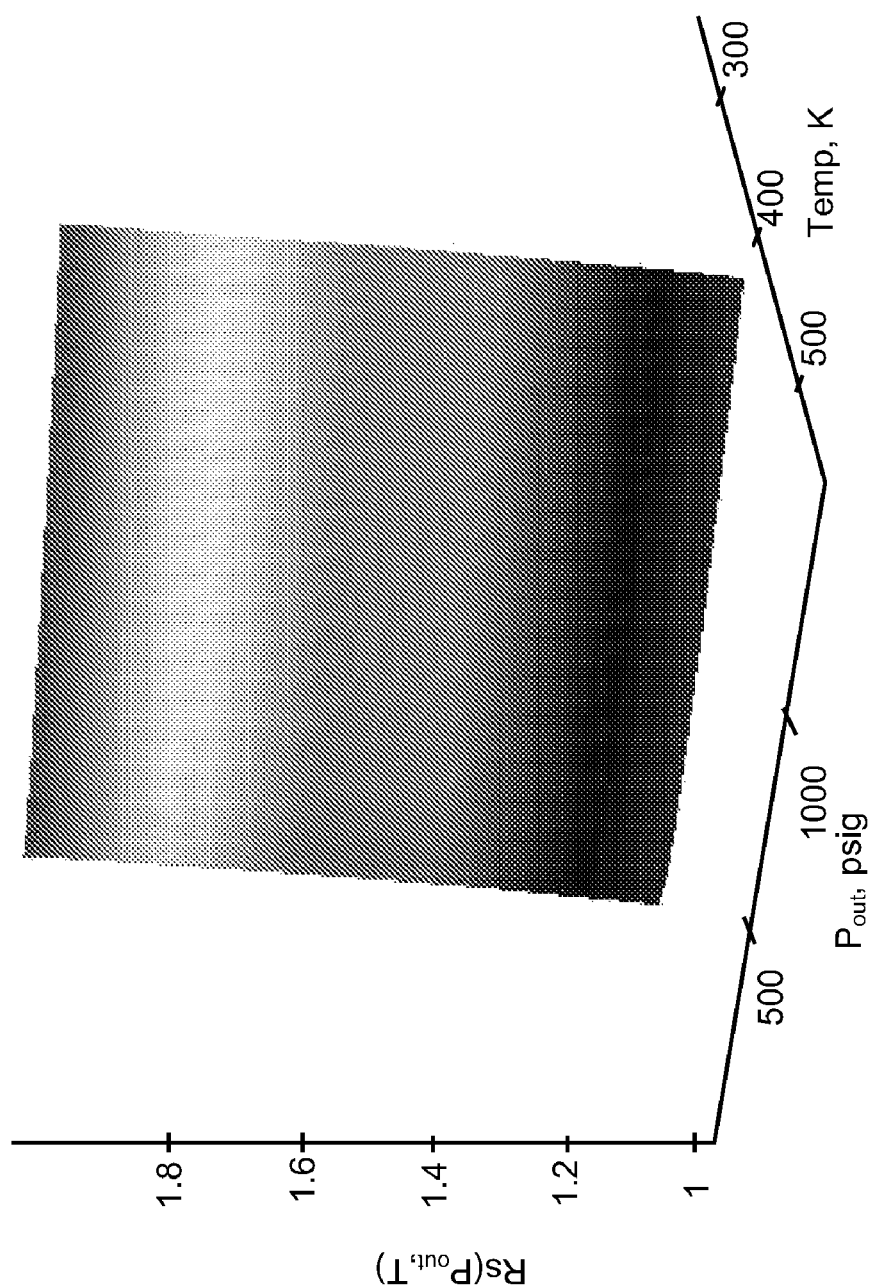

To explore the sensitivity of peaks resolution from retention coefficients the computation is performed when retention coefficient does not have pressure influence and when retention coefficient drops on 50% in its value when pressure reaches 100 atm at any temperature. Results are presented in Table 1 which shows resolution of n-hexane and n-heptane as a function of outlet pressure and temperature at different percentage drop of retention coefficient (10 m column length, 2 μm PDMS stationary phase thickness, 90 μm column radius, 423 K column temperature). FIGS. 7a and 7b are graphs showing sensitivity of peaks resolution as a function of outlet pressure and temperature for n-hexane and n-heptane. For FIGS. 7a and 7b, $b_k$ is equal to 0, and to −50% respectively, and the column length is 10 m with a 2 μm PDMS stationary phase thickness and 90 μm column radius.

TABLE 1

| Percentage | Pressure, psi | | |
| --- | --- | --- | --- |
|  | 14.7 | 147 | 1470 |
| 0% | 1.077 | 1.803 | 2.408 |
| 2% | 1.077 | 1.799 | 2.344 |
| 10% | 1.077 | 1.782 | 2.09 |
| 20% | 1.077 | 1.76 | 1.774 |
| 30% | 1.077 | 1.738 | 1.464 |
| 40% | 1.077 | 1.717 | 1.164 |
| 50% | 1.077 | 1.695 | 0.879 |

Computed results demonstrate that the change in partition coefficient due to pressure has very little change in resolution value at moderate pressures (less than 6% drop in resolution value) but in the case where it is assumed that partition coefficient will drop on 50% at 100 atm the results demonstrate that resolution will drop significantly (drop more than 60%) because of this pressure influence on retention factor. The decrease in retention factor should not exceed 10% (see, Wičar I, and Wičar II), and as can be seen from Table 1 at this condition the effect of pressure drop of retention factor is only 13% at 100 atm. Importantly, however, it has been found that peaks resolution improves by almost two times and as will be shown later the time of measurement will de reduced on two orders of magnitude. Note that at elevated pressure the carrier gas consumption will increase and which should be accounted for in the system design.

Temperature and pressure dependence of diffusion coefficient of octane in helium has been discusses. See, 10. K. V. Glagolev, A. N. Morozov, *Physical thermodynamics,* 2002, MSTU; Vandensteendam, Colette, and Piekarski, Salomon, *Measurement of the gaseous diffusion coefficients of a homologous series of compounds in helium. Temperature function of n-alkanes and methyl n-alkanoates,* Journal: C. R. Acad. Sci., Ser. C, 1972, Vol. 274, #25, P. 2032-2034; Eli, Grushka, and Virgil, R. Mayland, *Measurement of Diffusion Coefficients of Octane Isomers by the Chromatographic Broadening Method,* The J. of Physical Chemistry, Vol. 77, #11, 1973, P. 1437-1442; L. S. Ettre, *Open tubular columns prepared with very thick liquid phase film I. Theoretical basis,* Chromatographia, Vol. 17, #10, P. 553-559; L. S. Ettre, G. L. McClure and J. D. Walters, *Open tubular columns prepared with very thick liquid phase film II. Investigations on column efficiency,* Chromatographia, Vol. 17, #10, P. 560-569 (hereinafter "Ettre");

E. N. Fuller, J. C. Giddings, *A comparison of methods for predicting gaseous diffusion coefficients,* Journal of Gas Chromatography, July, 1965, P. 222-227 (hereinafter "Fuller"); Cussler E. L., *Diffusion: Mass transfer in fluid system,* 2nd edition, 1997; *Chemistry laboratory manual,* 2006; G. L. Hargrove and D. T. Sawyer, *Determination of Gaseous interdiffusion coefficients for solute vapor-carrier gas pairs,* Analytical Chemistry, Vol. 39, #2, 1967, P. 244-246; T. R. Marrero and E. A. Mason, *Gaseous Diffusion Coefficients,* J. Phys. Chem. Ref. Data, Vol. 1, #1, 1972, P. 3-118; and A. C. Frost, *A method for the measurement of binary gas diffusivities,* PhD. Thesis, Ann Arbor, Mich., 1967.

The diffusion coefficient equals:

$$0.248_{-12\%}^{+21\%} \text{ (cm}^2\text{/sec)}$$

for n-octane is selected for computation:

$$D_{C_8H_{18}-He} = 0.248 \cdot \frac{1}{p} \cdot \left(\frac{T}{303.15}\right)^{1.8} \text{ (cm}^2\text{/sec)},$$

and using an Ettre and Fuller approach extended to other n-alkanes that are experimentally investigated.

At low pressure the binary diffusion coefficient and outlet pressure product will be constant. At high pressure this product will no be longer constant and will need to be checked. An estimation method proposed by Takahashi in *The properties of gases and liquids,* B. E. Poling, J. M. Prausnitz, J. P. O'Connell. —5th ed., 2001 (hereinafter "Poling") is used in the computation. According to the model, critical temperature and pressure for the mixture will determine the value of correlation function $f(T_r, P_r)$:

$$\frac{D_{AB} \cdot P}{(D_{AB} \cdot P)|_{low-pressure}} = f(T_c, P_c) \qquad (13)$$

$$T_r = \frac{T}{T_c} \qquad (14)$$

$$T_c = y_a \cdot T_{cA} + y_b \cdot T_{cB} \qquad (15)$$

$$P_r = \frac{P}{P_c} \qquad (16)$$

$$P_c = y_a \cdot P_{cA} + y_b \cdot P_{cB}, \qquad (17)$$

where critical value for temperature and pressure are taken from Poling. Because in the analyzable mixture helium concentration is dominated (99% or more) the influence of other components can be omitted. For helium, critical temperature is equal to 5.19 K and critical pressure is equal to 2.27 bar. Because of such a low critical temperature even at high pressure, the product $D_{AB} \cdot P$ can be considered as a constant according to Takahashi model.

A few literature sources are available on diffusion coefficients in different stationary phases. For example, see M. M. van Deursen, *Novel concepts for fast capillary gas chromatography*, PhD thesis, Technische Universiteit Eindhoven, 2002; and A. H. Vorob'ev, *Diffusion questions in chemical kinetics*, 2003, MSU. However, in the approach described herein, an empirical relationship between diffusion coefficient in liquid and gas phases is used:

$$\frac{D_m}{D_{st}} \cong 5 \cdot 10^4 - 1 \cdot 10^5 \quad (18)$$

at STP and the pressure and temperature dependence for diffusion coefficient in stationary phase is used in the next form:

$$D_{C_8H_{18}-PDMS} = 4.8 \cdot 10^{-6} \cdot \frac{T}{303.15}$$

There are available data describing change in viscosity at high pressure (see, John V. Hinshaw, Leslie S. Ettre, *The variation of carrier gas viscosities with temperature*, Journal of High Resolution Chromatography, Vol. 20, #9, P. 471-481; and *NIST reference fluid properties*, ver. 7.0, 2002) and these data can be approximate with next equation:

$$\eta(T, p) \cong \quad (19)$$
$$20 \cdot \left(\frac{T}{300}\right)^{0.67742} + (3.148 - 3.075 \cdot 10^{-3} \cdot T) \cdot 10^{-3} \cdot p \; [\mu Pa \cdot sec],$$

where temperature in Kelvin unit and pressure in atmospheres.

From this equation it can be seen that in the range 1-100 atm at the constant temperature the viscosity value will not change more than 2% at high temperature (300-500 K) and in the first approximation we can omit this dependence (although this dependence is included in computation). Knowing the temperature and pressure influence on different parameters in equations 8, 10, and 11 their effect on GC performance can be evaluated.

Figure 8:
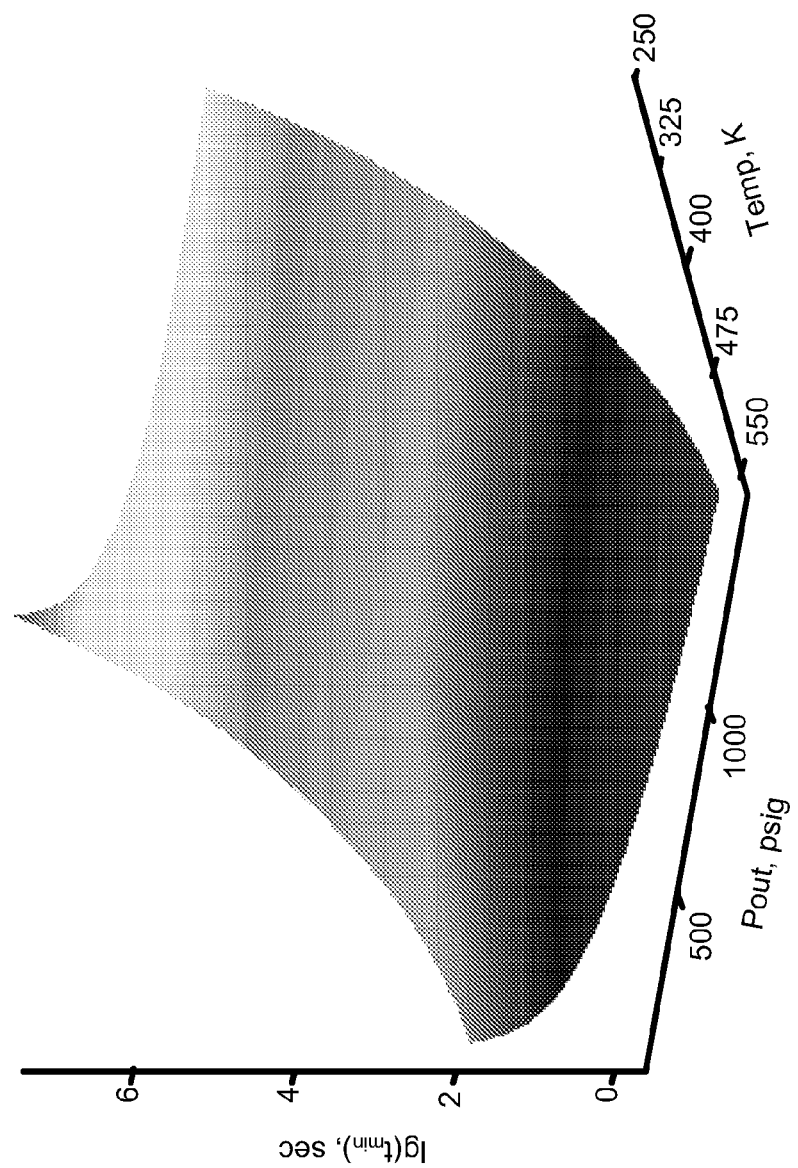
FIG. 8 is a graph showing the influence of pressure and temperature on minimum time required to perform gas chromatography analysis.

As mentioned, both pressure and temperature significantly decrease time of measurement. FIG. 8 is a graph showing the influence of pressure and temperature on minimum time required to perform gas chromatography analysis. It is assumed that the last component is a n-decane. A 10 m column length, 2 μm PDMS stationary phase thickness, and 90 μm column radius was used for the data shown in FIG. 8. Table 2 shows time of measurement for the mixture where n-tetradecane is the last eluted component as a function of outlet pressure and temperature at different percentage drop of retention coefficient. A 10 m column length, 2 μm PDMS stationary phase thickness, 90 μm column radius, and 423 K column temperature were used.

TABLE 2

| Percentage | Pressure, psi | | |
|---|---|---|---|
| | 14.7 | 147 | 1470 |
| 0% | 741.26 sec | 74.175 sec | 7.466 sec |
| 2% | 741.26 sec | 74.046 sec | 7.323 sec |
| 10% | 741.26 sec | 73.529 sec | 6.751 sec |
| 20% | 741.26 sec | 72.884 sec | 6.037 sec |
| 30% | 741.26 sec | 72.238 sec | 5.322 sec |
| 40% | 741.26 sec | 71.593 sec | 4.607 sec |
| 50% | 741.26 sec | 70.947 sec | 3.892 sec |

According to the presented results there is very strong dependence of time of experiments from temperature and pressure. Increasing temperature by 100 degrees from 373 K to 473 K reduces time of measurement by more than 24 times. Increasing pressure from 1 atm to 100 atm will leads to a reduction of measurement time by 110 times.

The peaks resolution is one of the most significant parameters characterizing the results of analysis. The high speed gas chromatography with low resolution will not provide information that is needed for downhole fluid characterization.

As mentioned, equation (11) (the "Purnell equation") can be used to describe the influence of pressure and temperature on resolution. Equation (11) can be divided on three parts. The first part is the efficiency term and it is related to peak width. The second part is selectivity part that refers to the relative spacing between peaks. And the last part is the retention part that refers to the value of retention coefficient (at low retention coefficient the resolution is tend to become zero and increasing retention coefficient improves resolution). Temperature negatively affects all parts of the Purnell equation and should be kept at as low as is practical. At the same time, pressure increases the number of theoretical plates, although this has very little effect on the second and the third parts of the Purnell equation. In general, resolution will be improved, as shown in FIGS. 7a and 7b, by increasing pressure up to an optimal value. However, increasing temperature can significantly decrease the peaks resolution. For example at 1 atm outlet pressure at isothermal conditions increasing temperature form 373 K to 473 K leads to peaks resolution drop from 3.9 to 0.3.

Figure 9A:
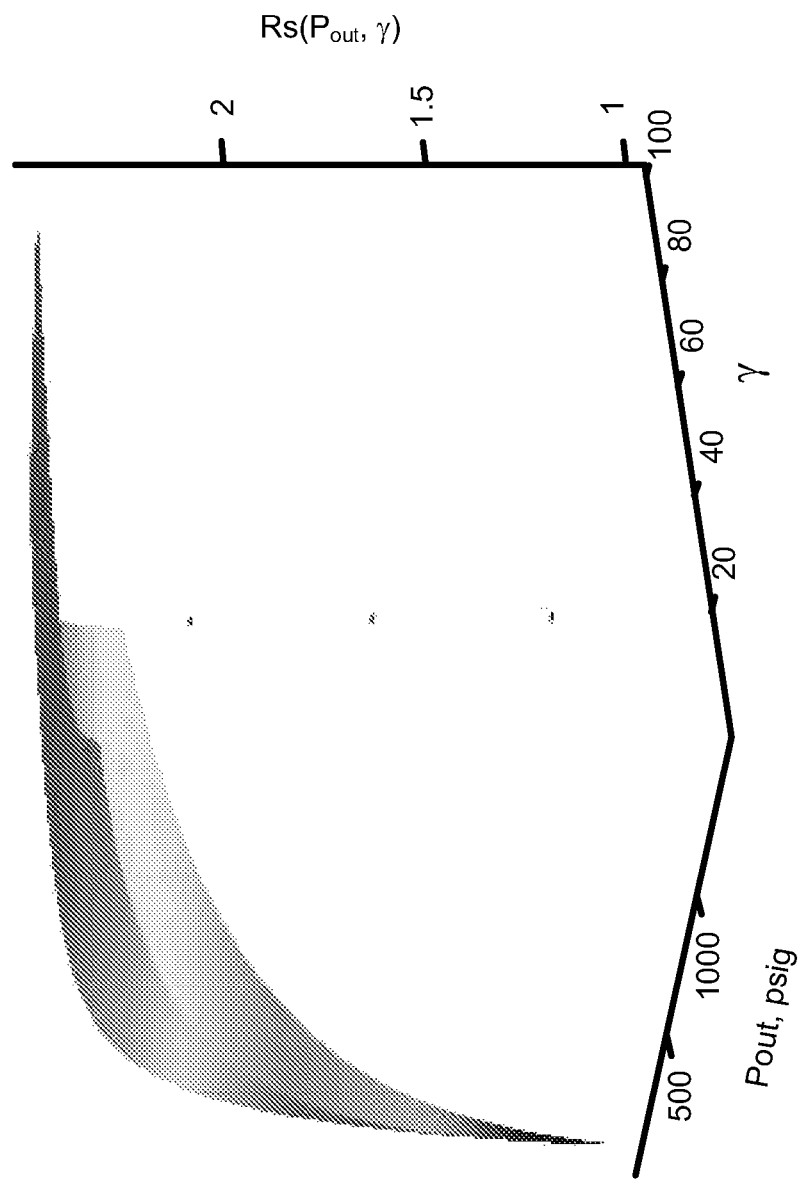
FIGS. 9a and 9b are graphs showing the influence of outlet pressure and inlet/outlet pressure ratio on resolution.
Figure 9B:
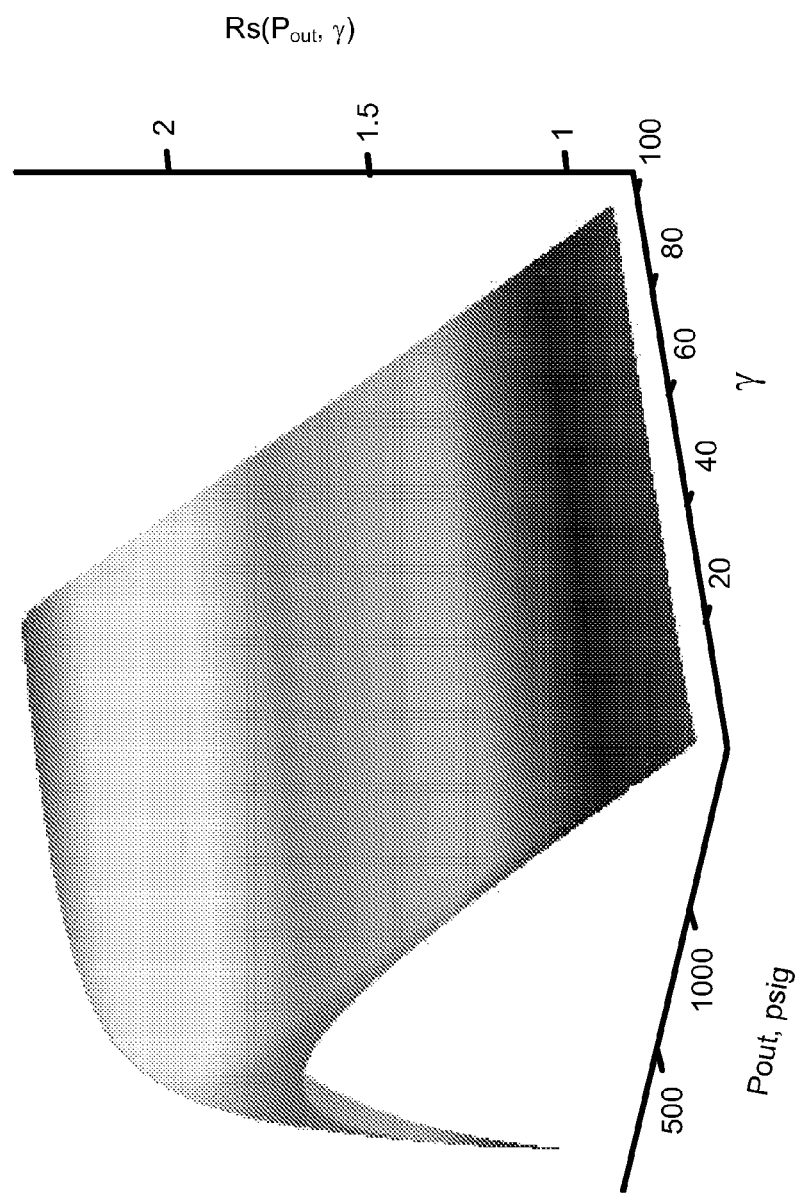

FIGS. 9a and 9b are graphs showing the influence of outlet pressure and inlet/outlet pressure ratio on resolution. In this example, α is used for n-hexane and n-heptane A 10 m column length, 2 μm PDMS stationary phase thickness, 90 μm column radius, and 473 K column temperature was used. In FIG. 9a, the partition coefficient K drops by 0%, and in FIG. 9b the partition coefficient K drops by 50%, both at 100 atm. From FIGS. 9a and 9b, it can be seen that there are conditions when there is an optimal value for the outlet pressure and inlet/outlet pressure ratio: the higher outlet pressure the lower inlet/outlet pressure ratio should be to get maximal value for peaks resolution.

The GC system design should also be modified when performing GC analysis at elevated pressure and temperature. According to embodiments, injector and detector volumes should be restricted to avoid significant negative influence on GC performance.

The sample volume (injector volume; exactly the same consideration can be done for detector volume) is calculated assuming that the extra-column dispersion introduced by injector will be equal to 5% from column dispersion: $\sigma_{sample}^2 = 0.05 \cdot \sigma_{column}^2$. Considering a rectangular distribution of the sample at the front of the column that will provide variance equal to $V_{sample}^2/12$ which will be added to column variance $V_{ret}/\sqrt{N}$ we will get:

$$\frac{V_{sample}^2}{12} + \left(\frac{V_{ret}}{\sqrt{N}}\right)^2 = 1.05 \cdot \left(\frac{V_{ret}}{\sqrt{N}}\right)^2 \quad (20)$$

and final expression will be:

$$V_{sample} \cong 2.419 \cdot \frac{L_{column} \cdot R_{column}^2 \cdot (1+k)}{+\sqrt{N}}. \quad (21)$$

Table 3 shows injector/detector volume as a function of outlet pressure and temperature at different percentage drop of retention coefficient. A 10 m column length, 2 µm PDMS stationary phase thickness, 90 µm column radius, and 423 K column temperature were used.

TABLE 3

| | Pressure, psi | | |
|---|---|---|---|
| Percentage | 14.7 | 147 | 1470 |
| 0% | $2.031 \cdot 10^{-3}$ cm$^{-3}$ | $1.221 \cdot 10^{-3}$ cm$^{-3}$ | $0.920 \cdot 10^{-3}$ cm$^{-3}$ |
| 2% | $2.031 \cdot 10^{-3}$ cm$^{-3}$ | $1.220 \cdot 10^{-3}$ cm$^{-3}$ | $0.919 \cdot 10^{-3}$ cm$^{-3}$ |
| 10% | $2.031 \cdot 10^{-3}$ cm$^{-3}$ | $1.216 \cdot 10^{-3}$ cm$^{-3}$ | $0.885 \cdot 10^{-3}$ cm$^{-3}$ |
| 20% | $2.031 \cdot 10^{-3}$ cm$^{-3}$ | $1.211 \cdot 10^{-3}$ cm$^{-3}$ | $0.842 \cdot 10^{-3}$ cm$^{-3}$ |
| 30% | $2.031 \cdot 10^{-3}$ cm$^{-3}$ | $1.206 \cdot 10^{-3}$ cm$^{-3}$ | $0.798 \cdot 10^{-3}$ cm$^{-3}$ |
| 40% | $2.031 \cdot 10^{-3}$ cm$^{-3}$ | $1.201 \cdot 10^{-3}$ cm$^{-3}$ | $0.754 \cdot 10^{-3}$ cm$^{-3}$ |
| 50% | $2.031 \cdot 10^{-3}$ cm$^{-3}$ | $1.197 \cdot 10^{-3}$ cm$^{-3}$ | $0.709 \cdot 10^{-3}$ cm$^{-3}$ |

Figure 10:
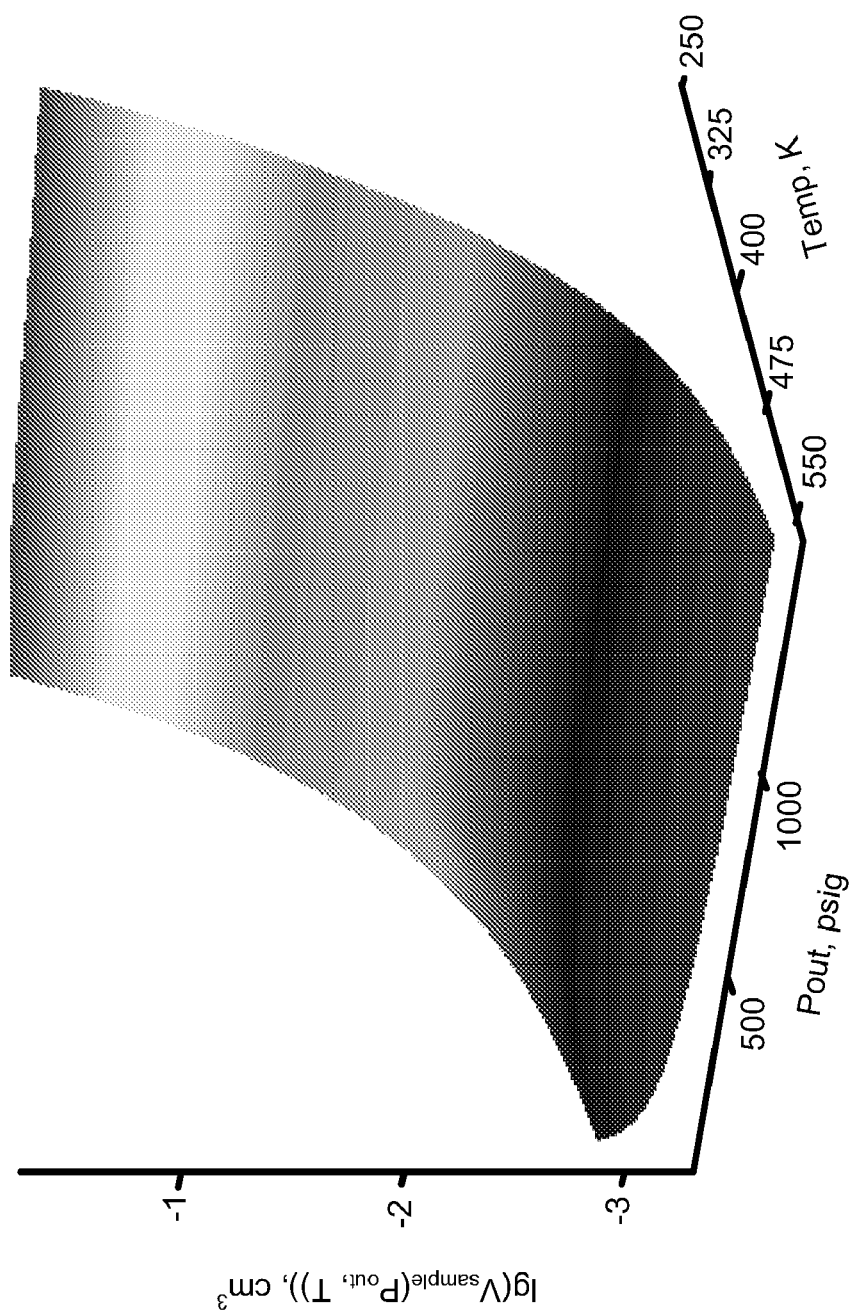
FIG. 10 is a graph showing influence of pressure and temperature on sample volume.

FIG. 10 is a graph showing influence of pressure and temperature on sample volume. A 10 m column length, and 2 µm PDMS stationary phase thickness where used.

From the presented analysis it can be seen that going from 1 atm to 100 atm leads to the injector/detector volume reduction by 23%, at the same time if temperature is elevated from 373 K to 473 K the injector/detector volume should be decreased in more than two times.

From the described numerical experiments the following GC system parameters should be selected to minimize time is required to perform GC analysis and maximize peaks resolution. These recommendations are presented in the Table 4 and Table 5. The ↑ symbol means that it is beneficial to increase this parameter and ↓ symbol means that it is desirable to minimize the value of this parameter. For and inlet/outlet pressure ratio there is optimums that provide maximum value for the peaks resolution.

TABLE 4

Optimization with Golay equation for circular column

| Parameter | GC analysis time Minimize | Resolution Maximize | Peak width Minimize |
|---|---|---|---|
| Outlet pressure | ↑ | ↑ | ↑ |
| Inlet/outlet pressure ratio | ↑ | Optimum | ↑ |
| Temperature | ↑ | ↓ | ↑ |
| Partition coefficient value | ↓ | ↑ | ↓ |

TABLE 5

Optimization with Spangler equation for SLS rectangular column

| Parameter | GC analysis time Minimize | Resolution Maximize | Peak width Minimize |
|---|---|---|---|
| Outlet pressure | ↑ | ↑ | ↑ |
| Inlet/outlet pressure ratio | ↑ | Optimum | ↑ |
| Temperature | Optimum | ↓ | Optimum |
| Partition coefficient value | ↓ | ↑ | ↓ |

From the evaluations it has been found that pressure and temperature modify the GC performance in many ways. Going to elevated pressures allow performing GC analysis much faster at slightly lower peaks resolution that can be compensated with optimum column design. At isothermal GC experiments to maximize the peaks resolution the minimum practical temperature should be selected. This minimum will be determined by resolution number that needs to be achieved in experiment and depending on the analyzable mixture complexity. Also, it has been found that increasing temperature decreases the time required for the experiments. The positive effects of temperature on GC performance can be maximized and negative influence minimized when temperature programming GC analysis performed instead of isothermal analysis at isothermal conditions.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, while some of the embodiments described herein refer to gas chromatography, the present invention is also applicable to other types of chromatographic analysis such as liquid chromatography and supercritical fluid chromatography. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for high pressure gas chromatographic analysis of a fluid sample, the system comprising: a pressure balanced tool housing constructed and adapted for deployment in a wellbore in a subterranean rock formation; a fluid collection system for obtaining the fluid sample downhole; a mobile gas phase of a controllable mobile gas phase source in communication with a controllable expander injector coordinately maintains the fluid sample at pressures similar to a pressure of the subterranean rock formation from which the fluid sample was collected; a flowpath adapted to flow the mobile gas phase and the fluid sample at pressures above 20 atmospheres and at ambient temperatures above 100 degrees Celsius and the controllable expander injector is adapted to convert the fluid sample into a gas phase to inject the fluid sample into the flowpath as a gas; a separation column adapted to operate at high pressures, forming part of the flowpath downstream of the controllable expander injector, for separating a plurality of components within the fluid sample; a detector located downstream of the separation column, measuring at least one property of the gas, thereby generating measurement data representing properties of at least one component of the fluid sample, wherein the flowpath, the controllable expander injector, the separation column and the detector are housed within the tool housing and adapted to operate at pressures approximate to the incoming downhole pressure of the fluid sample from which the fluid sample was collected; and a processor adapted to calculate from the measurement data a value relating to the amount of at least one component of the fluid sample.

2. The system according to claim 1, wherein the system is adapted to operate at pressures above about 20 atmospheres.

3. The system according to claim 1, wherein the system is adapted to operate at pressures above about 100 atmospheres.

4. The system according to claim 1, wherein the system is adapted to operate at ambient temperatures above 100 degrees Celsius.

5. The system according to claim 1, further comprising:
a heating and cooling device that is capable of providing variable temperatures to the separation column.

6. The system according to claim 1, further comprising a tap in fluid communication with a surface flowline carrying produced fluids and said controllable expander injector.

7. The system according to claim 6, wherein the system is in close proximity a wellhead of the wellbore.

8. The system according to claim 7, wherein the tap is located on the surface flowline prior to any significant pressure drop in the produced fluids after the wellhead.

9. The system according to claim 1, further comprising a container adapted to contain the fluid sample at high pressure, and being in fluid communication with the controllable expander injector.

10. The system according to claim 1, wherein the separation column is not a packed column.

11. The system according to claim 1, wherein the calculated value relating to the at least one component is selected from a group consisting of: mass concentration of a component, volume concentration of a component, and ratio of components.

12. A method for high pressure gas chromatographic analysis of a fluid sample containing a plurality of components, the method comprising the steps of: obtaining the fluid sample with a fluid collection system utilizing a pressure balanced tool housing in a wellbore in a subterranean rock formation; using a mobile gas phase of a controllable mobile gas phase source in communication with a controllable expander injector that coordinately maintains the fluid sample as pressure similar to a pressure of the subterranean rock formation from which the fluid sample was collected; flowing the injected fluid sample through a separation column; detecting a property of the fluid sample in the flow path with a detector thereby generating measurement data; and calculating from the measurement data a value relating to the amount of at least one component of the fluid sample, wherein the flowpath, the controllable expander injector, the separation column and the detector are housed within a tool housing and adapted to operate at pressures approximate to the incoming downhole pressure of the fluid sample from which the fluid sample was collected.

13. The method according to claim 12, wherein the flowpath is adapted to operate at pressures above about 20 atmospheres.

14. The method according to claim 12, wherein the flowpath is adapted to operate at pressures above about 100 atmospheres.

15. The method according to claim 12, wherein the flowpath is adapted to operate at ambient temperatures above 100 degrees Celsius.

16. The method according to claim 12, further comprising the step of collecting the fluid sample downhole wherein said steps of injecting, flowing and detecting are carried out downhole.

17. The method according to claim 12, wherein collecting the fluid sample and said steps of injecting, flowing and detecting are carried out in close proximity to the wellbore.

18. The method according to claim 17, wherein said step of collecting the fluid sample is carried out at a location on a surface flowline prior to any significant pressure drop in produced fluids from the wellbore.

19. The method according to claim 12, further comprising the steps of: containing the fluid sample at high pressure within a container; and flowing the fluid sample from the container to the controllable expander injector.

20. The method according to claim 12, wherein the separation column is not a packed column.

21. The method according to claim 12, wherein the calculated value relating to the at least one component is selected from a group consisting of: mass concentration of a component, volume concentration of a component, or ratio of components.

22. A system of for high pressure chromatographic analysis of a fluid sample, the system comprising: a pressure balanced tool housing constructed and adapted for deployment in a wellbore in a subterranean rock formation; a fluid collection system for obtaining the fluid sample downhole; a mobile gas phase of a controllable mobile gas phase source in communication with a controllable expander injector coordinately maintains the fluid sample at pressures similar to a pressure of the subterranean rock formation from which the fluid sample was collected; a flowpath adapted to flow a mobile phase and the fluid sample at pressures above about 20 atmospheres; controllable expander injector adapted to convert the fluid sample into a gas phase to inject the fluid sample into a flowpath as a gas; a separation column adapted to operate at pressures above about 20 atmospheres, forming part of the flowpath downstream of the controllable expander injector, for separating a plurality of components within the fluid sample, wherein the separation column is not a packed column; and a detector located downstream of the separation column, the detector adapted to measure properties of the fluid sample, wherein the flowpath, the controllable expander injector, the separation column and the detector are housed within the tool housing, and adapted to operate at pressures approximate to the incoming pressure of the fluid sample from which the fluid sample was collected.

23. The system according to claim 22, further comprising a processing system adapted calculate from measurements made by the detector a value relating to the amount of at least one component of the fluid sample.

24. The system according to claim 23, wherein the calculated value relating to the at least one component is selected from a group consisting of: mass concentration of a component, volume concentration of a component, or ratio of components.

25. The system according to claim 22, wherein the system is adapted to operate at pressures above about 100 atmospheres.

26. The system according to claim 22, wherein the system is adapted to operate at ambient temperatures above 100 degrees Celsius.

27. The system according to claim 22, further comprising:
a tool housing constructed and adapted to be deployed in a wellbore in a subterranean rock formation; and
a fluid collection system for obtaining the fluid sample downhole, wherein the injector, column and detector are housed within the tool housing and adapted to operate under downhole conditions.

28. The system according to claim 22, further comprising a tap in fluid communication with a surface flowline carrying produced fluids and said controllable expander injector.

29. A system for downhole chromatographic analysis of a fluid sample, the system comprising: a pressure balanced tool housing constructed and adapted to be deployed in a wellbore in a subterranean rock formation; a fluid collection system for obtaining the fluid sample downhole; a mobile gas phase of a controllable mobile gas phase source in communication with a controllable expander injector coordinately maintains the fluid sample at pressures similar to a pressure of the subterranean rock formation from which the fluid sample was collected; a flowpath adapted to flow the mobile gas phase and the fluid sample at pressures above 20 atmospheres and at ambient temperatures above 100 degrees Celsius, and the controllable expander injector is adapted to convert the fluid sample into a gas phase to inject the fluid sample into the flowpath as a gas; a separation column forming part of the flowpath downstream of the controllable expander injector, for separating a plurality of components within the fluid sample; and a detector housed within the separation column located downstream of the separation column, the detector adapted to measure properties of the fluid sample, wherein the flowpath, the controllable expander injector, the separation column and the detector are housed within the tool housing and adapted to operate at pressures approximate to the incoming downhole pressure of the fluid sample from which the fluid sample was collected.

30. The system according to claim 29, wherein the tool housing forms part of a wireline toolstring adapted to be deployed in the wellbore via a wireline cable.

31. The system according to claim 29, further comprising a processing system adapted calculate from measurements made by the detector a value relating to the amount of at least one component of the downhole fluid sample.

32. The system according to claim 31, wherein the calculated value relating to the at least one component is selected from a group consisting of: mass concentration of a component, volume concentration of a component, or ratio of components.

33. The system according to claim 31, wherein the processing system is adapted to remain on the surface while the tool housing is deployed in the wellbore, and the processing system is in communication with the tool housing through at least a communication cable.

34. The system according to claim 29, wherein the system is adapted to operate at pressures above about 20 atmospheres.

35. The system according to claim 29, wherein the system is adapted to operate at ambient temperatures above 100 degrees Celsius.

36. A system for chromatographic analysis of a fluid sample at high ambient temperatures, the system comprising: a pressure balanced tool housing constructed and adapted to be deployed in a wellbore in a subterranean rock formation; a fluid collection system for obtaining the fluid sample downhole; a mobile gas phase of a controllable mobile gas phase source in communication with a controllable expander injector coordinately maintains the fluid sample at pressures similar to a pressure of the subterranean rock formation from which the fluid sample was collected; a flowpath adapted to flow the mobile gas phase and the fluid sample at pressures above 20 atmospheres and the controllable expander injector is adapted to convert the fluid sample into a gas phase to inject the fluid sample into the flowpath as a gas; a separation column forming part of the flowpath downstream of the controllable expander injector, for separating a plurality of components within the fluid sample; and a detector located downstream of the separation column, measuring at least one property of the gas, wherein the flowpath, the controllable expander injector, the separation column and the detector are all adapted to operate at ambient temperatures above 75 degrees Celsius, wherein the flowpath, the controllable expander injector, the separation column and the detector are housed within a tool housing and adapted to operate at pressures approximate to the incoming downhole pressure of the fluid sample from which the fluid sample was collected.

37. The system according to claim 36, wherein the flowpath, the controllable expander injector, the separation column and the detector are all adapted to operate at ambient temperatures above 100 degrees Celsius.

38. The system according to claim 36, wherein the flowpath, the controllable expander injector, the separation column and the detector are all adapted to operate at ambient temperatures above 150 degrees Celsius.

39. The system according to claim 36, wherein the flowpath, the controllable expander injector, the separation column and the detector are all adapted to operate at pressures above 100 atmospheres.

40. The system according to claim 36, further comprising:
a tool housing constructed and adapted to be deployed in a wellbore in a subterranean rock formation; and
a fluid collection system for obtaining the fluid sample downhole, wherein the flowpath, injector, column and detector are housed within the tool housing and adapted to operate under downhole conditions.

41. The system according to claim 36, further comprising a processing system adapted to calculate from measurements made by the detector a value relating to the amount of at least one component of the fluid sample.

42. A method for chromatographic analysis of a fluid sample at high temperatures, the method comprising the steps of: converting the fluid sample into a gas phase with a controllable expander injector to inject the fluid sample as a gas into a high pressure flowpath, wherein the flow is adapted to operate at pressures above about 20 atmospheres and operate at ambient temperatures about 100 degrees Celsius; flowing the injected fluid sample through a separation column; controlling the temperature of at least the separation column such that the initial temperature of the separation column when the fluid sample enters the separation column is at least 100 degrees Celsius, and the temperature is substantially increase while at least part of the fluid sample remains within the separation column; and detecting a property of the fluid sample in the flow path with a detector thereby generating measurement data, wherein the flowpath, the controllable expander injector, the separation column and the detector are housed within the tool housing and adapted to operate at pressures approximate to the incoming downhole pressure of the fluid sample from which the fluid sample was collected.

43. The method according to claim 42, wherein the separation column temperature is at least 125 degrees Celsius when the sample enters the separation column.

44. The method according to claim 42, wherein the separation column temperature is at least 150 degrees Celsius when the fluid sample enters separation the column.

45. The method according to claim 42, wherein the flow-path is adapted to operate at pressures above about 100 atmospheres.

46. The method according to claim 42, further comprising the steps of: containing the fluid sample at high pressure within a container; and flowing the fluid sample from the container to the controllable expander injector.

47. The method according to claim 42, further comprising collecting the sample from a surface flowline from a wellhead wherein said steps of injecting, flowing and detecting are carried out in close proximity to the wellhead.

48. The method according to claim 42, further comprising the step of collecting the sample downhole wherein said steps of injecting, flowing and detecting are carried out downhole.

* * * * *